United States Patent
Linn et al.

(10) Patent No.: US 9,734,287 B2
(45) Date of Patent: Aug. 15, 2017

(54) LINKING HEALTH CARE APPLICATIONS FOR INFORMATION MANAGEMENT

(71) Applicant: IMS Health Incorporated, Danbury, CT (US)

(72) Inventors: Stefan Clemens Linn, New York, NY (US); John Diarmuid MacCarthy, Bourne end (GB); Seth David Reid, London (GB)

(73) Assignee: Quintiles IMS Incorporated, Danbury, CT (US)

( * ) Notice: Subject to any disclaimer, the term of this patent is extended or adjusted under 35 U.S.C. 154(b) by 278 days.

(21) Appl. No.: 13/826,189

(22) Filed: Mar. 14, 2013

(65) Prior Publication Data
US 2014/0244296 A1    Aug. 28, 2014

Related U.S. Application Data

(60) Provisional application No. 61/770,042, filed on Feb. 27, 2013.

(51) Int. Cl.
G06Q 50/22    (2012.01)
G06Q 50/24    (2012.01)
G06F 19/00    (2011.01)

(52) U.S. Cl.
CPC .......... G06F 19/322 (2013.01); G06F 19/327 (2013.01)

(58) Field of Classification Search
CPC ........ G06Q 50/22; G06Q 10/10; G06Q 50/24; G06Q 10/06; G06Q 10/00
See application file for complete search history.

(56) References Cited

U.S. PATENT DOCUMENTS

2007/0061393 A1*  3/2007  Moore ................ G06F 17/3089
                                                                  709/201
2013/0054467 A1*  2/2013  Dala ..................... G06F 19/322
                                                                  705/51

* cited by examiner

*Primary Examiner* — Maroun Kanaan
(74) *Attorney, Agent, or Firm* — Fish & Richardson P.C.

(57) ABSTRACT

The disclosure generally describes computer-implemented methods, software, and systems for managing information exchange between medical care applications and an analytical infrastructure for medical care information. The disclosure also describes implementations that manage user access to medical care applications and communications between medical care applications.

21 Claims, 7 Drawing Sheets

LINKING HEALTH CARE APPLICATIONS FOR INFORMATION MANAGEMENT

CROSS-REFERENCE TO RELATED APPLICATIONS

This application claims the benefit of U.S. Provisional Application No. 61/770,042, filed Feb. 27, 2013, which is incorporated herein in its entirety by reference.

BACKGROUND

Wireless phones have been very popular devices with consumers. A wireless phone may download one or more applications from an application store to their wireless phone and invoke one or more application. Examples of applications include games, photo editing software, and social networking applications. Sometimes applications designed specifically for mobile deployment on mobile operating systems are referred to as "apps." However, the term application refers in general to any program that a computing device may execute that includes a series of instructions to accomplish a given task. Sometimes, tasks that users want to accomplish are tasks related to health care and medical treatment. Some applications may be developed specifically for use by various parties in managing information related to health care tasks, such as helping a patient to monitor a condition, allowing a doctor to gather and analyze information to treat patients more effectively, or allowing health care companies, such as pharmaceutical companies, to aggregate data and draw conclusions that support their business.

OVERVIEW

The present disclosure relates to computer-implemented methods, software, and systems for controlling the distribution of medical care applications that interface with an analytical infrastructure. The present disclosure also relates to implementations that facilitate secure information interchange between medical care applications and medical information processing by the analytical infrastructure.

One computer-implemented method includes providing a user with access to a first medical application on a mobile device, wherein the first medical application is relevant to a medical condition of the user; receiving medical data, wherein at least a portion of the medical data is received from the user via the first medical application at an information gateway provided by the mobile device, the medical data comprising private information relevant to the medical condition; transmitting the medical data to a secure information repository for subsequent use in generating a conclusion related to the medical condition of the user; identifying a second medical application that is relevant to the medical condition of the user; authenticating the second medical application to provide access for the second medical application to the medical data at the secure information repository; sharing the medical data with the authenticated second medical application; and using the medical data by the second medical application to generate a conclusion related to the medical condition of the user.

Other implementations include corresponding computer systems, apparatus, and computer programs recorded on one or more computer storage devices, each configured to perform the actions of the method. A system of one or more computers can be configured to perform particular operations or actions by virtue of having software, firmware, hardware, or a combination of software, firmware, or hardware installed on the system that in operation causes or causes the system to perform the actions. One or more computer programs can be configured to perform particular operations or actions by virtue of including instructions that, when executed by a data processing apparatus, cause the apparatus to perform the actions.

The foregoing and other implementations can each optionally include one or more of the following features. In some implementations, the conclusion aids in the treatment of the medical condition of the user. In such implementations, the conclusion may be one of: a diagnosis, a determination that a user should begin a particular therapy, a determination that a user should cease a particular therapy, a determination that the user should alter a plan of care, a determination that the user should access a medical care application to treat a medical condition, or a determination that the user should schedule an appointment with a medical professional. In other implementations, the conclusion may be information that helps a participant in the health care process to make a health decision In some implementations, the conclusion is based at least in part comparing the medical data for the user to de-identified aggregated medical data obtained for other users.

In some implementations the first medical care application may be associated with a particular pharmaceutical compound, a particular medical condition, a particular pharmaceutical manufacturer, or a particular health care professional. In other implementations, at least a portion of the medical information is obtained from data received from at least one of: an electronic medical records system, a medical claims records system, a retail pharmacy records system, a health care professional records system, a pharmaceutical company records system, or a sensor communicatively coupled to the mobile computing device.

The subject matter described in this specification can be implemented in particular implementations so as to realize one or more of the following helpful features. First, medical applications may be provided for a user, by a physician, a wireless device provider, a carrier, a hospital or pharmacist, or by one or more of these entities working in association with one another. Alternatively, users may be able to access medical applications that they consider relevant to health concerns that they confront. These applications may promote and facilitate the use of medical information from a variety of sources to derive meaningful conclusions that might not otherwise be made. Secondly, the aspects of limitations in which applications are distributed can aid in the deployment of applications to help patients manage medical conditions. Thirdly, the information may be provided in a way that prevents the inadvertent release of information.

Other implementations may provide other helpful features. For example, some implementations may provide access to a medical care application portal. Such a medical care application portal may provide helpful features such as facilitating secure information interchange between applications so that a user may be provided access to one application by the medical care application portal, and subsequently the user may provide information to the portal by interacting with the application. The portal may then provide a secure, centralized infrastructure for gathering and sharing health care information between applications. As part of this sharing process, a second application may be provided to the user so that the second application may be authenticated to have access to the health care information. The second application may subsequently be able to use the health care information in useful ways. One way in which the second application may make use of the health care information is to aid in the treatment of the original user. However, it will be recognized that other parties besides the original user may be provided with access to the second application in order to derive meaningful conclusions from the health care information. For example, other parties may be able to use the second application to use the health care information to help them make business decisions or diagnostic and treatment decisions. The many ways in which the health care information may be used will be discussed in greater detail, below, but in general the health care information also allows other participants in the health care process to meet economic or other goals. For example, a pharmaceutical company may use the information to aid in marketing, an insurer may use the information to aid in cost-savings measures, and governmental agencies may use the information to aid in law enforcement applications.

The details of one or more implementations of the subject matter of this specification are set forth in the accompanying drawings and the description below. Other features, aspects, and advantages of the subject matter will become apparent from the description, the drawings, and the claims.

DETAILED DESCRIPTION

Figure 1:
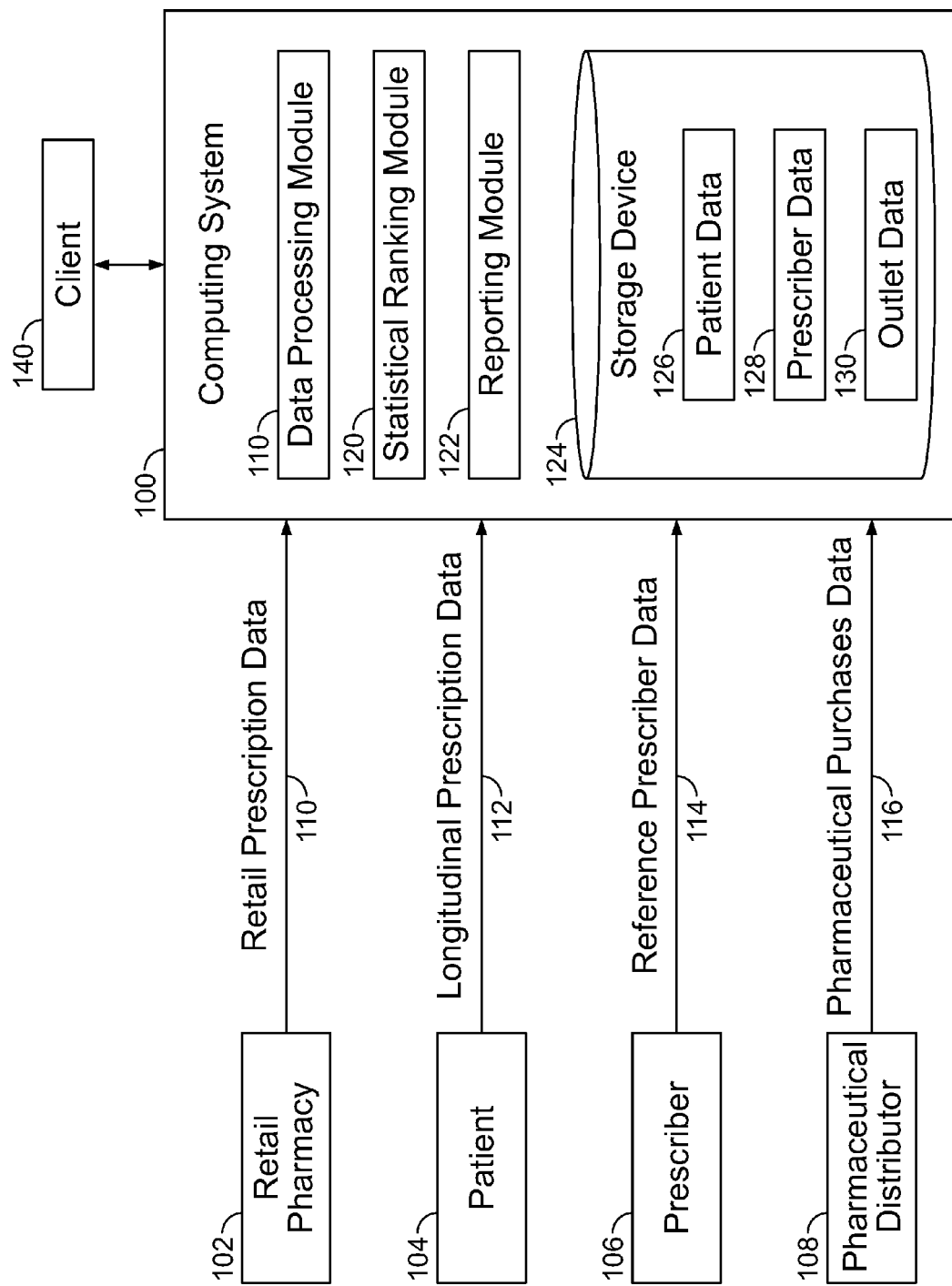
FIG. 1 illustrates an example medical care application distribution system implemented in a computing system 100 configured for integrating de-identified data for analytical purposes.

This disclosure generally describes computer-implemented methods, software, and systems for distributing health-care related applications and enabling the health-care related applications to interface with each other and with an analytic and reporting infrastructure. The health-care related applications are generally intended to be executed on mobile computing devices. As part of their operation, the applications gather data. When the applications subsequently interface with an analytic and reporting infrastructure, that data allows them to derive medically meaningful conclusions that can assist patients in obtaining treatment and caregivers in providing care. In one set of implementations, the subject of this disclosure may involve a medical care application portal that manages access to the health-care related applications. The portal may provide security when accessing the health-care related applications. The portal further manages information interchange between the health-care related applications. For example, such information interchange may involve gathering data at a first application, and then accessing the data at a second application to derive conclusions based on the data from the first application In certain mobile environments, it is not possible for applications to interact with one another directly. Implementations may provide a way of dealing with this problem in that it becomes possible to gather information from a first application to which access is provided by a portal, use the portal to transmit the information for centralized storage, and subsequently accessing the centralized information storage for use by another application. As part of this access process, it is possible to integrate security measures that ensure that even as applications are able to share information with one another, the information sharing is done in a secure way.

Applications, in general, include sets of instructions that are executed by a computing device that provide functionality. However, applications may take various forms. Some applications may be exclusively local applications that are run by a computing device and request resources from a desktop operating system. However, other applications may be executed by a mobile operating system. Yet other applications may be provided through web browsers, such as by scripting, plug-ins, or other browser extensions and add-ons that allow browsers to provide hosting capability for applications. Sometimes applications are distributed, so that their functionality is provided by multiple machines, for example in a client-server or peer-to-peer distributed architecture. Distributed functionality may be especially important in implementations in which clients are mobile devices that individual users employ to interact with an analytic platform that runs on one or more servers.

Many of the applications that are available for wireless phones and similar mobile computing devices are medical or health-related applications. Such applications may have many types of functionality that address medical or health-related problems. Using medical and health-related applications can have a wide variety of benefits for users. Users may include people or entities involved in the healthcare deployment process, and different applications might be intended for different groups of users. A medical doctor might use an application to manage medication that stores a database of drug interactions, while a patient might use an application that records and organizes information about that patient's blood sugar levels. Pharmaceutical manufacturers may distribute applications related to the medications they sell. A pharmaceutical company that sells hypertension drugs might provide an application that tracks blood pressure measurements.

Furthermore, it is desirable to provide applications with the ability to share information with one another. Information sharing can aid in treatment of patients with multiple diagnoses, especially diagnoses whose treatment interrelates. For example, an obese patient may suffer not only from diabetes, but also from hypertension. It may be advantageous to give that patient access to an application to a blood sugar tracking application, and coordinate information provided by that application with information provided by a blood pressure tracking application. Such related information may be of use not only to a patient, but also to treatment providers. For example, a physician may want to have access to blood sugar measurements that a patient takes using an application in order to determine what blood sugar medication is the best choice for that patient. However, other parties may benefit in various ways from sharing information. For example, an insurance company may be able to examine aggregated information from a variety of users and determine ways to save money based on that aggregated information. For example, an insurance company may be able to track how many individuals taking different statins were subsequently hospitalized with myocardial infarctions, and by performing this analysis, determine not only what the best treatment outcomes are, but also which drugs are the most cost-effective to prescribe to patients. Thus information sharing can allow implementations to generate conclusions, such as to improve patient health outcomes or to help in business decisions.

Such applications gather information that is necessary to perform their functions. For example, an application may monitor blood sugar levels and use that information to alert a user when he or she needs to take a dose of insulin. However, information about a user's blood sugar levels might also be relevant to a doctor who wishes to prescribe a blood sugar medication, or to a pharmaceutical company who is trying to market a blood sugar medication.

For illustration purposes, the various implementations described herein will be described with regard to a medical care application distribution system that receives data regarding patients, prescribers, and pharmaceutical retailers and rates these stakeholders with regard to the sale/distribution of one or more medical care applications. As discussed above, such a medical care application distribution system may be integrated into a medical care application portal system that distributes medical care applications in order to facilitate information sharing to derive conclusions from information received by medical care applications. Such a system is also designed to preserve confidentiality, privacy, and secrecy of such information by controlling how such information is accessed. As will be described in greater detail below, the system provides wholesalers, retailers, and prescribers of the one or more medications, which may include controlled substances, with a broad view of the market of the one or more medical care applications at both a local and national level. Such an information ecosystem may assist in integrating medical information in a meaningful way by participants in the healthcare process because the information ecosystem gathers data to derive conclusions by analyzing pieces of data that are not generally available together as a basis for decision-making and healthcare recommendations. Thus, implementations discussed herein allow individual patients and healthcare providers to make better healthcare decisions on a small scale by facilitating secure information interchange between applications, but the implementations also facilitate aggregation of information on a larger scale so that market participants can perceive patterns based on behaviors and data related to larger populations of participants in the healthcare system.

An applications environment may be configured to link an intelligent database and collection system with a mobile application (and application market) where the applications in the application market are configured to report and transmit information into the database and its collection system. The application may include an application configured to run on a wireless device or tablet, including things such as an iPad, iPhone or an Android handset. However, these are simply examples of devices that may run an application, and in general a wide range of computing devices are appropriate for use in various implementations in which users of mobile devices interact with a centralized application market and analytic infrastructure. As noted above, an aspect of such mobile devices is that there may be restrictions with respect to the ability of these applications to share information with one another. Hence, implementations provide ways to help facilitate information sharing between applications by gathering data through a first application, transmitting the data to a secure, centralized location, and subsequently authorizing access to that data for another application that can derive analytic conclusions based on the data.

These applications may be prescribed by a doctor and there may be an authentication or credentialing system that is necessary in order for a consumer to access a particular application. A doctor may prescribe an application that assists a patient in pain management, which in turn provides that information to a physician so that the physician may better prescribe pain management pharmaceuticals. In such an example, another piece of relevant information is that some of the pain management pharmaceuticals may be heavily regulated or greatly controlled substances, such as due to the possibility for abuse. These aspects of implementation will be discussed in greater depth, below. Additionally, applications may be prescribed by another party in the process that is aware of which applications are germane to the user. For example, a pharmacist who provides a user with a medication for epilepsy may also have a suggestion for an application for another neurological issue, or an insurer may have a suggestion that they would like to facilitate transitioning a user from an expensive brand-name medication to a generic drug. Alternatively, a pharmaceutical company may provide an app that is designed to complement the administration of a drug they produce, as will be discussed in greater depth, below.

Generally the application environment includes a wireless device or tablet that may be used by a consumer or user. In addition there may be an application that also has a desktop or laptop component. It may be noted that the "wireless" aspect of a computing device in an implementation is not intended as limiting, and computing devices that are not easily portable may be used where appropriate and devices that are portable may communicate with some of the other portions of an implementation by using a wired connection. In general, the relevance of this aspect of the design is that the portal is hosted at a device for a user, and that the device communicates with centralized infrastructure that stores and manages information for subsequent usage and analysis.

The functionality across user devices may vary with their dimensions. There may be a limited subset of data in a mobile computing device while a more expansive subset is available across a desktop environment. Such division of functionality may be due to greater computing resources at a desktop machine than a mobile computing device due to the space, physical interface, and power limitations of the mobile computing device. In addition, the application may utilize certain authentication, confidence and/or security measures that are available through a wireless device. For example, a wireless device may be designated as belonging to a particular user. However, individual users may be associated with specific accounts that are further associated with privacy settings.

Because a developer may know that a wireless handset consumer with an account with a particular national wireless carrier may have a line of credit, that determination may be used to provide an assurance level that is not necessarily be available across other platforms, such as desktops. These confidence measures may be used to offer an expansive array of products and services. However, other conventional security means such as a password, which may be a one-time password, biometrics, a pattern and so forth may be required in an implementation to establish the identity of a user before they are given access privileges such as the ability to make a purchase of a medical application. These security measures may be especially important because medical data can be quite sensitive and it may be important to protect the privacy and confidentiality of participants in the healthcare process. While it is necessary for private information to be available where it is needed, it is of paramount importance that only parties who are entitled to access private information have access to it, so as to comply with legal standards and so that parties who should not have access to private information are unable to exploit the information to the detriment of patients or other holders of private information.

The wireless device may be configured to interface with an intermediary. The intermediary may include one or more servers that run a healthcare application store. When providing access to applications, the medical application portal may interface with such a healthcare application store to aid in the distribution of the applications. Many mobile operating systems have application stores associated with applications available for that operating system, with the application store being maintained by the creators of the operating system. The portal may interface with such an application store to help provide access to such applications as it distributes the applications. These application stores may work with pharmacists, physician's offices, and medical care providers in order to allow the user device to access one or more of these applications.

Access to the applications and information related to the applications may be secured depending on a patient's condition. As discussed briefly above, the wireless devices and the intermediary may provide other technologies that are designed to safeguard personal identifiable information and shield the inadvertent release of personally identifiable and sensitive information, particularly in those circumstances where there is a stigmatic condition or issue involved. The application may be addressed to a particular condition or treatment regimen, such as a pharmaceutical compound or treatment regimen. Alternatively, the application may include a diagnostic component and/or interface with a Bluetooth diagnostic component that may produce diagnostic measurement information, such as blood sugar and other parameters. It may be noted that Bluetooth is only one type of interface for diagnostic components and other approaches are possible. In addition, the application market may interface with physician systems, payer systems (e.g., such as insurers and government regulatory systems) and in addition may also provide information to other proxies such as healthcare informatics companies that process this information in order to ascertain data such as pharmaceutical efficacy. For example, blood cholesterol levels may be used to assess if a user's treatment regimen is working properly if the user was prescribed a statin.

The application store and the application may be coupled to an analytic engine so that a pharmaceutical company and the physicians they work with may distribute more timely or updated treatment regimens and also ascertain pharmaceutical efficacy. In addition, the application and its server-side components may also interface with a physician decision support system in order to identify a treatment regimen. The application and its server components may also interface with insurer regimens that can perform cost-saving measures so that generic pharmaceuticals are explored before the more expensive brand name pharmaceutical is prescribed and that once the less expensive treatment regimen has been pursued the consumer may automatically be upgraded into the next level of pharmaceutical benefit that would be available, such as a pharmaceutical that is only available in brand form. The pharmaceutical information exchanged may also include information that assists a user in condition management as well. The information may include information about aspects of how a user responded to a treatment in the past, such as efficacy data or side-effect incidences.

In one configuration, the secure mobile application platform and the application store are provided by a physician-related server. In another configuration, the platform is provided by a pharmaceutical company server and yet in another environment the platform is operated by a trusted intermediary and/or a government regulatory agency. Additionally, the application store may act as an aggregator that manages access to applications provided from a variety of sources. Various additional information about the configuration of the platform will be discussed in connection with FIG. 7, below.

The application server may work in association with analytic services to ascertain efficacy and/or to offer suggestions to a physician to better treat a condition. Such feedback and analytics may be offered as a value added service and/or may be subject to privacy and opt-in controls or may include a physician who elects to receive treatment recommendations as the data is processed. The application and its data may be protected by one or more privacy measures. Data may be encrypted and/or undergo an anonymization filter so that the data is coupled to key information as it is processed throughout the system. However, once the data leaves the user's handset, the data may be processed in such a way that no personally identifiable information is available. Such processing is also known as sanitizing the data, and it allows retaining enough information to obtain meaningful conclusions from aggregated data without jeopardizing user privacy. Along these lines, communicating the data may require and employ various encrypted communications across a data network so that the information remains in compliance with HIPAA and other privacy requirements. Thus, data may be processed on a private basis for individualized recommendations, or it may be aggregated and sanitized so as to allow data analysis for populations.

The infrastructure may be centrally located or the subset information may be configured to reside in a distributed manner. The system may also configured with a Food and Drug Administration (FDA) credentialing server to present risks to patients if the applications do not work as intended and/or the products that are being treated do not work as intended so that the application and/or underlying treatment regimen can be subject to a market-wide recall.

The application may be coupled to a loyalty regimen so that pharmaceutical companies may offer loyalty programs in order to persuade a consumer to stay with a particular treatment regimen rather than switch to an alternative treatment regimen. For example, a pharmaceutical company may offer coupons for a brand-name drug that is an alternative to a generic formulation of the drug or another, cheaper drug in order to maintain its customer base. It is important to maintain privacy in the context of loyalty regimens or other marketing steps taken on the basis of user information. It may be necessary for the user to positively opt-in to receive marketing communications or at least allow the user to opt out. However, if a user is receptive to receiving such communications, it can be mutually beneficial to a user and a drug company to allow the drug company to market to a user based on characteristics of their symptoms and treatment.

The application may include pharmaceutical drug information, drug interaction information, adherence reminders, information that documents and allows a patient to record which treatment regimen has been done and may be coupled to one or more peripheral sensors that are designed to test and diagnose certain conditions. Data may be gathered for the application by a sensor camera and/or one or more physical wireless or wired attachments. The application may also even distribute drug safety alerts and also offer travel assistance if a particular prescription has to be administered by a nurse or other licensed healthcare professional. In some cases, the application may also coordinate and identify an available medical opportunity so that the person may have an appointment with a physician at their earliest opportunity in order to follow-up on a particular condition. From an analytical perspective, the identified data may include one or more pieces of descriptive information such as a patient identifier, a doctor identifier, a diagnosis, a pair identifier, a particular prescription and may be integrated so that an analytic service provider may monitor data across a larger population. This integration may in turn allow various stakeholders in the process such as physicians, pharmaceutical companies and insurers to better identify patient reported outcomes, costs and savings efficacy, home diagnostics data and track outcomes. The integration also allows pharmacists to perceive the extent to which the consumers are refilling drugs, ascertain loyalty data and also offer enriched pharmacy services such as eye test appointments and vaccinations.

The system may allow insurers and other payers to provide integrated care management, offer some preventative treatment measures, perform member benefit management and also perform disease prevention. The application may be coupled to an electronic medical record system as well so that information is automatically populated in one or more electronic medical records that may be distributed across the Internet. The analytics and/or application store may also include a secure cloud repository so that if a wireless device is lost or misplaced, the user is able to replicate their configuration upon activating a new wireless device in their stead. As noted, the wireless device may be involved in two-way transmission of data from the electronic medical records provider.

In one configuration, the application environment may be used to set reminders for drugs or appointments, secure those next appointments, automatically launch refills, request refills, and schedule an appointment with a physician so that a sensitive prescription can be automatically refilled. Thus, the environment may include functionality in which specific administrative actions are taken by a healthcare provider to care for a patient. The application may include a selectively evocable pharmacist link within the application in order to allow a pharmacist to activate one or more components there. Applications may be used to manage a variety of conditions. There may be a constituent application to manage asthma while there is another application to manage other conditions as well. In addition, the application may include a catalog of other modules within a larger application so that the user may load an application in order to manage pain and further involve modules that work together to address that issue. For example, part of the application may track medication usage while another application may help a user with breathing exercises.

The application may be linked to other applications on a user device such as a wireless phone. For example, it may set calendar reminders in a calendar or scheduling application, it may set reminders in a reminder engine, it may trigger an alarm to notify a user, such as by playing an audio signal or by vibrating, or it may load location information into a mapping database, such as from a GPS or another location sensor. The application may also include an editable list of reminders.

FIG. 1 illustrates an example medical care application distribution system implemented in a computing system 100 configured for integrating de-identified data for analytical purposes. The computing system may be implemented as a data processing apparatus that is capable of providing the functionality discussed herein, and may include any appropriate combination of processors, memory, and other hardware and software that can receive appropriate medical data and process the data as discussed below. At a high-level, the illustrated example computing system 100 receives various data from sources that are participants in the healthcare process. The sources may include retail pharmacies 102, patients 104, prescribers 106, and pharmaceutical distributors 108. The data may include retail prescription data 110, longitudinal patient data 112, reference prescriber data 114, and pharmaceutical purchase data 116.

FIG. 1 illustrates the process by which an analytical infratrstructure is able to integrate data received about an individual, either via the mobile application from patients 104 or from their healthcare provider, who may act as a prescriber 106, with other data sources available in IMS, such as pharmacies 102 and pharmaceutical distributors 108. The data from patient 104 is not restricted to longitudinal patient data 112 but may include any health metrics recorded through their device and the data from the prescriber 106 could include a similar range of measures, recorded through their EMR system, as well as lab results or images. It is important to understand that the system will not store nominative data in an aggregated database but only de-identified data. Nominative data for an individual can be compared to the relevant aggregated data, but this will be achieved by using aggregated values in the individual patient application, not by keeping nominative records for multiple patients in a single database. Also, the integration of data from sources other than the user and their medical professionals can only be achieved on a de-identified basis except in the instance that the individual gives permission to use their identity information (name, location, gender and age) for the purpose of providing them with their information from another source, such as pharmaceutical purchase data 116 from pharmacies.

The retail prescription data 110 may include data regarding prescriptions dispensed in the retail sector, such as by retail pharmacies 102. The retail prescription data 110 may be received directly from one or more retail pharmacies 102 and represent data reflecting all pharmaceutical products dispensed by the one or more outlets 102, including information about the type of prescription used to obtain the product and the payment method used to purchase the product. As noted previously, this information may be sanitized and aggregated to protect patient privacy. The one or more retail pharmacies 102, which may include pharmacy chains, independent pharmacies, long-term care facilities, and/or mail services, may provide the retail prescription data 110 on a periodic basis (e.g., every week or month). Though FIG. 1 shows the retail prescription data 110 being provided directly from the one or more retail pharmacies 102 to the computing system 100, the retail prescription data 110 may be collected by one or more other intermediate systems and then provided to the computing system 100. If intermediate systems are used, the aggregation and sanitization of the retail prescription data 110 may potentially be performed by the intermediate systems.

The longitudinal patient data 112 may include sanitized retail patient-level data for the one or more patients 104. For example, the longitudinal patient data 112 may include information about retail pharmacy-sourced prescription insurance claims, retail pharmaceutical scripts, and/or patient profile data. Longitudinal patient data 112 includes information about aspects of care for the one or more patients 104. Though FIG. 1 illustrates the longitudinal patient data 112 as being received by the computing system 100 directly from one or more patients 104, the longitudinal patient data 112 may be collected by one or more other systems and then provided to the computing system 100 in a manner analogous to the similar approach discussed for retail prescription data 110. Moreover, the longitudinal patient data 112 may not originate from the one or more patients 104, but may rather be provided by one or more prescribers/physicians with whom a patient interacts, insurance companies to which a patient submits insurance claims, and/or retailers at which a patient purchases a pharmaceutical product.

The reference prescriber data 114 may include background information for one or more prescribers 106. For example, the reference prescriber data 114 may include a prescriber's demographic information, address, affiliations, authorization data (e.g., DEA, AOA, SLN, and/or NPI numbers), profession, and/or specialty. While most prescribers will be medical doctors, other healthcare professionals such as physician-assistants or nurse practitioners may also be prescribers 106. Though FIG. 1 illustrates the reference prescriber data 114 as being received by the computing system 100 directly from one or more prescribers 106, the reference prescriber data 114 may be collected by one or more other systems and then provided to the computing system 100 in a manner analogous to the similar approach discussed for retail prescription data 110. Moreover, the reference prescriber data 114 may not originate from the one or more prescribers 106, but rather be created and/or maintained by one or more other entities (e.g., government agencies or professional medical organizations) that track information about the prescribing behavior of prescribers 106.

The pharmaceutical purchase data 116 may include information about pharmaceutical purchases made from distributors 108 (e.g., pharmaceutical wholesalers or manufacturers). For example, the pharmaceutical purchase data 116 may include information about the outlet from which a pharmaceutical product is purchased, the type of pharmaceutical product purchased, the location of both the purchaser and seller of the pharmaceutical product, when the purchase was conducted, and/or the amount of a pharmaceutical product that was purchased. Though FIG. 1 illustrates the pharmaceutical purchase data 116 as being received by the computing system 100 directly from one or more distributors 108, the pharmaceutical purchase data 116 may be collected by one or more other systems and then provided to the computing system 100 in a manner analogous to the similar approach discussed for retail prescription data 110. Moreover, the pharmaceutical purchase data 116 may not originate from the one or more distributors 108, but rather be provided by the purchaser of the pharmaceutical product (e.g., a retail outlet).

The various types of data just discussed, which may include retail prescription data 110, longitudinal prescription data 112, reference prescriber data 114, and pharmaceutical purchases data 116, are received by computing system 100 in order to derive conclusions based on the data. As noted previously, by the time the data is received by computing system 100, it should have been sanitized so that the data does not include private or confidential information that computing system 100 should not able to access.

For illustrative purposes, computing system 100 will be described as including a data processing module 118, a statistical ranking module 120, a reporting module 122, and a storage device 124. However, the computing system 100 may be any computing platform capable of performing the described functions. The computing system 100 may include one or more servers that may include hardware, software, or a combination of both for performing the described functions. Moreover, the data processing module 118, the statistical ranking module 120, and the reporting module 122 may be implemented together or separately in hardware and/or software. Though the data processing module 118, the statistical ranking module 120, and the reporting module 122 will be described as each carrying out certain functionality, the described functionality of each of these modules may be performed by one or more other modules in conjunction with or in place of the described module.

The data processing module 118 receives and processes one or more of retail prescription data 110, longitudinal patient data 112, reference prescriber data 114, and pharmaceutical purchase data 116. In processing the received data, the data processing module 118 may filter and/or mine the retail prescription data 110, longitudinal patient data 112, reference prescriber data 114, and pharmaceutical purchase data 116 for specific information. The data processing module 118 may filter and/or mine the received retail prescription data 110, longitudinal patient data 112, reference prescriber data 114, and pharmaceutical purchase data 116 for specific pharmaceuticals. Thus, any received retail prescription data 110, longitudinal patient data 112, reference prescriber data 114, and pharmaceutical purchase data 116 that regards pharmaceutical products that are not classified as being associated with a tracked compound or prescription may be disregarded. For example, the received data may be processed by data processing module 118 so as to track use of a specific antibiotic, or of antibiotics in general.

After processing the received retail prescription data 110, longitudinal patient data 112, reference prescriber data 114, and pharmaceutical purchase data 116, the data processing module 118 aggregates the processed data into patient data 126, prescriber data 128, and outlet data 130. These groups of data may be stored in storage device 124. In some implementations, the data processing module 118 may create profiles for each patient, prescriber, and retail pharmacy outlet for which data is received.

Retail prescription data 110 may include information about a retail pharmacy outlet that dispenses one or more pharmaceutical products, information about one or more patients that purchased the pharmaceutical products, and information about one or more prescribers that wrote the scripts used by the patients to obtain the pharmaceutical products. In this example, data processing module 118 would add information contained in the received retail prescription data 110 into profiles associated with the retail outlet, the one or more patients, and the one or more prescribers. In another example, longitudinal patient data 112 may include information about a patient that received prescriptions for a pharmaceutical product and information about one or more prescribers from which the patient received the prescriptions. In this example, data processing module 118 would add information contained in the received longitudinal patient data 112 into profiles associated with the patient and the one or more prescribers.

In other implementations, the data processing module 118 may simply sort and store, in storage device 124, processed retail prescription data 110, longitudinal patient data 112, reference prescriber data 114, and pharmaceutical purchase data 116, the data processing module 118 for later use by other modules.

For each patient 104 with regard to whom data has been received, the patient data 126 may include any information related to the prescription and/or sale of one or more types of pharmaceutical products. Patient data 126 may include the quantity of each type of pharmaceutical product the patient has purchased, cumulative days' supply of a pharmaceutical product the patient should still have, cumulative dosage of a pharmaceutical product, medication possession ratio, the number and/or name of doctors from which the patient has received scripts, the number and/or name of retail outlets from which the patient has purchased pharmaceutical products, and/or information regarding the payment method(s) used by the patient when purchasing pharmaceutical products (e.g., cash or insurance).

For each prescriber 106 with regard to whom data has been received, the prescriber data 128 may include any information related to prescriptions written by the prescriber for one or more types of pharmaceutical products and the patients to whom the prescriptions were written. Prescriber data 128 may include the quantity of one or more types of pharmaceutical products for which the prescriber has written a prescription, the percentage of prescriptions for one or more types of pharmaceutical products written by a prescriber in relation to the total number prescriptions written by the prescriber, the percentage of prescriptions for one or more types of pharmaceutical products that are paid for with cash, and/or the number of patients for whom the prescriber has written a prescription for one or more types of pharmaceutical products and who currently have a supply of the one or more types of pharmaceutical products that exceeds a threshold.

For each retail pharmacy outlet 102 with regard to which data has been received, the outlet data 130 may include any information related to the sales of one or more types of pharmaceutical products, patients to whom sales of one or more types of pharmaceutical products were made, and/or prescribers who wrote the scripts upon which the sales of one or more types of pharmaceutical products were based. For example, the outlet data 130 may include the quantity of one or more types of pharmaceutical products sold by the outlet, the percentage of sales of one or more types of pharmaceutical products in relation to the total sales by the retail outlet, and the percentage of sales of one or more types of pharmaceutical products that are paid for with cash.

The statistical ranking module 120 uses the patient data 126, prescriber data 128 and/or outlet data 130 to rate and rank individual patients, prescribes, and retail outlets. In some implementations, statistical ranking module 120 may compare one or more elements of the patient data 126 corresponding to a patient to averages of the one or more elements of the patient data 126 across a set of patients. Based on the comparison of the one or more elements of the patient data 126, the statistical ranking module 120 may assign one or more ratings to a patient. In other words, for each element of the patient data 126 (e.g., quantity of each type of pharmaceutical product the patient has purchased and percentage of purchases that were made with cash), the statistical ranking module 120 may assign a rating to a patient that reflects how an element of the patient data 126 compares to that same element of other patients in a set with respect to these calculated statistics. Patients in the set used in the comparison may be patients in the same location (e.g., country, state, city, or zip code), patients who share similar patient data (e.g., medical diagnosis or demographic information), and/or patients who share some other relationship.

The patient data 126 corresponding to a first patient may indicate that, over the last month, the first patient had a certain set of blood glucose readings. The patient data 126 may also indicate that, over the same time period, blood gluose reading that are typical for an average patient. Based on this information, the statistical ranking module 120 may ascertain that the first patient's blood glucose readings are abnormally high. This conclusion may lead to the suggestion that the user or the user's doctor, if authorized access to the blood glucose information, should be advised that the user's blood glucose is abnormal and may require a therapeutic response.

Similarly, the statistical ranking module 120 may compare one or more elements of the prescriber data 128 corresponding to a prescriber to averages of the one or more elements of the prescriber data 128 across a set of related prescribers. Based on the comparison of the one or more elements of the prescriber data 128, the statistical ranking module 120 may assign one or more ratings to a prescriber. Prescribers in the set used in the comparison may be prescribers in the same location (e.g., country, state, city, or zip code), prescribers who share similar professional data (e.g., practice area or demographic information), and/or prescribers who share some other relationship. The statistical ranking module 120 may be able to derive conclusions for prescribers from the prescriber data 128, in a manner similar to that used for the patient data. For example, it may determine that general practitioners in one county tend to prescribe generic drugs with patients with epilepsy, while neurologists are more likely to use branded drugs for their patients with a similar diagnosis. These determinations may, for example, be used to suggest that a pharmaceutical company should promote a new anticonvulsant more heavily to neurologists than to general practitioners.

The statistical ranking module 120 may also compare one or more elements of the outlet data 130 corresponding to a retail outlet to averages of the one or more elements of the outlet data 130 across a set of related retail outlets. Based on the comparison of the one or more elements of the outlet data 130, the statistical ranking module 120 may assign one or more ratings to an outlet. Retail outlets in the set used in the comparison may be retail outlets in the same location (e.g., country, state, city, or zip code), prescribers who share similar commercial data (e.g., size of the retail outlet), and/or prescribers who share some other relationship. For example, the data may indicate that certain drugs are more often bought at rural pharmacies, and other drugs are bought at urban pharmacies. For example, these determinations may suggest that pharmacies should stock more antihistamines for pollen allergies at their rural branches.

The ratings assigned to a patient, prescriber, and/or retail outlet by the statistical ranking module 120 may be normalized numbers that reflect the analysis performed with regard to an element of the patient data 126, prescriber data 128 and/or outlet data 130. In some implementations, the ratings determined by the statistical ranking module 120 may be updated on a periodic basis (e.g., weekly or monthly) or updated any time new data regarding the element corresponding to the rating is received by the computer system 100. Alternatively, in some implementations, the ratings determined by the statistical ranking module 120 may be calculated every time the statistical ranking module 120 receives a query for the ratings.

The statistical ranking module 120 may also calculate a composite rating for each patient, prescriber, and/or retail outlet for which data has been received by the computer system 100. In some implementations, the statistical ranking module 120 may weight each of the individual element ratings associated with a patient, prescriber, or retail outlet and apply an equation to calculate a composite of the individual element ratings. Alternatively, in some implementations, the statistical ranking module 120 may select a proper subset of the available individual element ratings and calculate a composite rating based on the selected individual element ratings.

In some implementations, the statistical ranking module 120 may rank patient, prescriber, and/or retail outlet with respect to one another based on the determined ratings. For example, the statistical ranking module 120 may rank all of the patients in a given location (e.g., a zip code) based on each patient's composite rating. Such an approach allows consideration of patient information for a population in a specific location, which is helpful because the patient behavior of interest may be for a localized population. In another example, the statistical ranking module 120 may rank all of the prescribers who are oncologists in a given state based on each prescriber rating related to the quantity of one or more types of pharmaceutical products for which the prescriber has written a prescription (i.e., an element of the prescriber data 128). Such an approach may be useful because specialists may prescribe differently than generalists and it may be of interest to compare the care strategies used by these different groups of prescribers, as discussed above.

The reporting module 122 prepares reports based on the ratings and/or rankings calculated by the statistical ranking module 120. The reports prepared by the reporting module 122 may include one or more of the ratings calculated by the statistical ranking module 120 as well as any other data contained in the patient data 126, prescriber data 128 and/or outlet data 130. For example, a report generated by the reporting system may include composite ratings for all prescribers in a given state for a particular pharmaceutical product (e.g., oxycodone—a controlled substance).

The system shown may be filtered and/or mined based on any one or more criteria associated with a patient, prescriber, and/or retail outlet. The reports may be filtered and/or mined based on location, type pharmaceutical product, medical specialty of a prescriber, category of a retail outlet (e.g., large chain retail outlet), and or one or more ratings calculated by the statistical ranking module 120. In other words, any data received and processed by the data processing module 118 or any ratings or rankings calculated by the statistical ranking module 120 may be included in or used to filter and/or mine the data included in a report.

Additionally, in some implementations, the reports generated may be either dynamic or static. The reporting module 122 may generate a report that includes data presented in one or more static formats (e.g., a chart, a graph, or a table) without providing any mechanism for altering the format and/or manipulating the data presented in the report. In such an implementation, the data presentation is generated and saved without incorporating functionality to update the data presentation. In some implementations, the reporting module 122 provides a static report in a PDF, spreadsheet, or XML format. Such a format generally provides an understanding of the reporting module 122 as textual data or a visualization, but other forms of presenting conclusions such as audio, video, or an animation are not excluded as potential results from reporting module 122.

Additionally or alternatively, the reporting module 122 may generate a report that includes controls allowing a user to alter and/or manipulate the report itself interactively. For example, the reporting system may provide a dynamic report in the form of an HTML document that itself includes controls for filtering, manipulating, and/or ordering the data displayed in the report. Moreover, a dynamic report may include the capability of switching between numerous visual representations of the information included in the dynamic report. In some implementations, a dynamic report may provide direct access as selected by a user to some or all of the patient data 126, prescriber data 128 and/or outlet data 130 prepared by the data processing module 118 and/or the statistical ranking module 120, as opposed to allowing access to only data and/or ratings included in the report itself.

One or more clients 140 may interface with the computing system 100 to request and receive reports created by the reporting system. In some implementations, the one or more clients 140 may include a web browser that provides Internet-based access to the computing system 100. Through the web browser, a user of a client 140 (e.g., a wholesaler, a retail outlet, or a prescriber) may request a static or dynamic report from the reporting system as discussed above.

In some implementations, access to the computing system 100 may be controlled in order to protect any confidential data stored in the computing system 100. In some implementation, each user of a client 140 that attempts to request a report from the computing system 100 may be required to create and log into a user account. The user accounts may include identifying information about the user that may be used to limit the user's access to particular types of data, reports, and/or other functionality. A user account associated with a prescriber may limit the prescriber to only viewing prescriber rating data for prescribers in his/her area and/or patient rating data for the patient's with which the prescriber has a professional relationship. Moreover, the user account associated with a prescriber may limit may limit the level of detail of the data included in a report to prevent the prescriber from accessing another prescriber's private data. Additional aspects related to access will be discussed, below, with respect to FIG. 7.

There may be any number of clients 140 associated with, or external to, the example computing system 100. While the illustrated example computing system 100 is shown in communication with one client 140, alternative implementations of the example computing system 100 may communicate with any number of clients 140 suitable to the purposes of the example computing system 100. Further, the term "client" and "user" may be used interchangeably as appropriate without departing from the scope of this disclosure. Moreover, while the client 140 is described in terms of being used by a single user, this disclosure contemplates that many users may share the use of one computer, or that one user may use multiple computers.

The illustrated client 140 is intended to encompass any computing device such as a desktop computer, laptop/notebook computer, wireless data port, smartphone, personal digital assistant (PDA), tablet computing device, one or more processors within these devices, or any other suitable processing device. For example, the client 140 may comprise a computer that includes an input device, such as a keypad, touch screen, or other device that can accept user information, and an output device that conveys information associated with the operation of the computing system 100. The input device may be used by client 140 to provide instructions to computing system 100 that computing system 100 can execute to provide information requested by client 140 from the various data that computing system 100 receives.

In some implementations, functionality described as being performed by the computing system 100 may be performed by the client 140. For example, the computing system 100 may provide a client 140 with direct access to the ratings and rankings calculated by the statistical ranking module 120. As a result, some or all of the functionality described as being performed by the reporting module 122 may be performed locally by the client 140.

Figure 2:
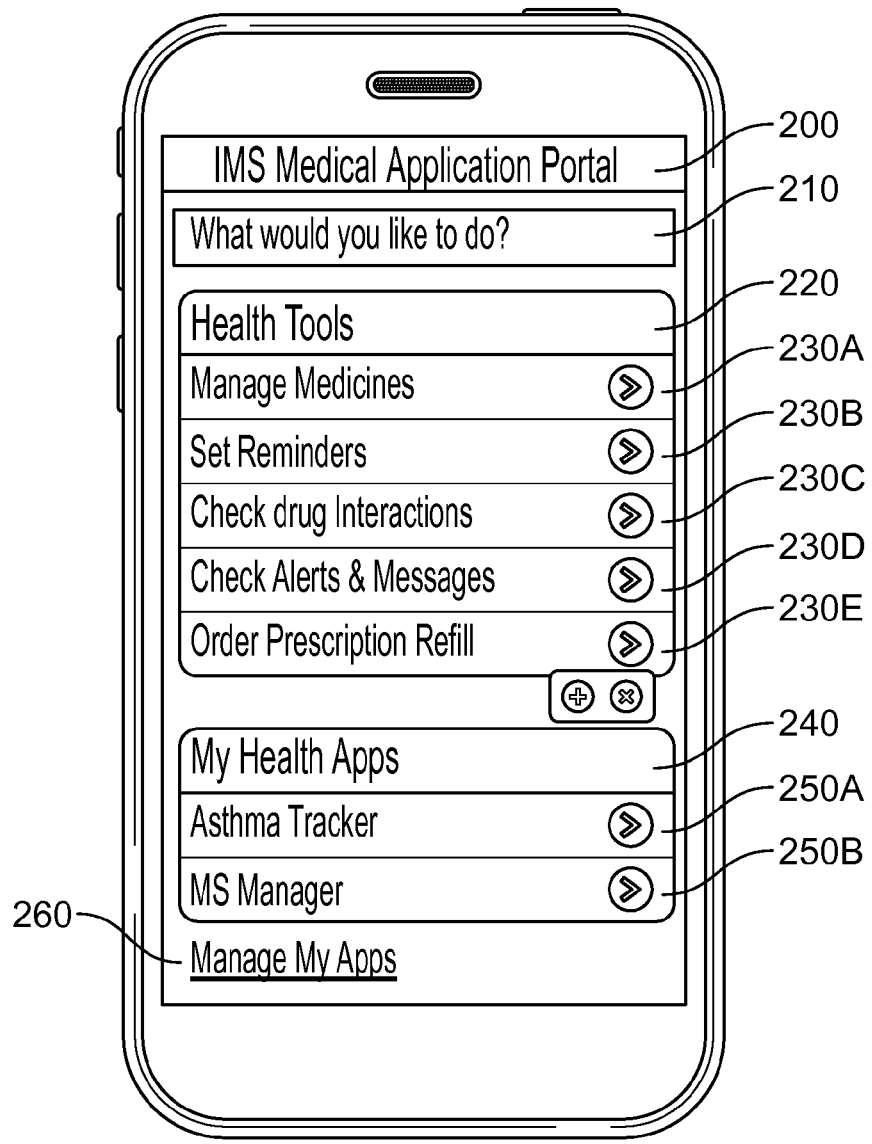
FIG. 2 is a screen shot from a medical care application that resides on a wireless device.

FIG. 2 is a screen shot from a medical care application that resides on a wireless device. The medical care application is a portal that provides a user with access to commands that allow the user to manage and request healthcare information and services. In FIG. 2, the medical care application is identified as IMS Medical Application Portal 200. The screen shot shows a user prompt 210 asking the user, "What would you like to do?" IMS Medical Application Portal provides several commands that the user may select to obtain healthcare information and services. The first set of commands is a set of Health Tools 220. These commands provide basic functions that will be of use to most users. These commands may include manage medicines 230A, set reminders 230B, check drug interactions 230C, check for alerts & messages 230D, and order prescription refills 230E. However, the medical care application (IMS Medical Application Portal 200) is further configured to interface with applications specific to the particular user, user's apps 240. In the FIG. 2, these other applications include Asthma Tracker 250A and MS Manager 250B. These example applications illustrate that the applications may be branded, such as being received from a specific pharmaceutical manufacturer. The IMS Medical Application Portal application 200 may receive information from these other applications and report it to a computing device 100 for analysis of this information, as discussed with respect to FIG. 1. FIG. 2 also illustrates an option of Manage My Apps 260 that will be discussed in more detail in the discussion of FIG. 4. FIG. 2 is an example of the interface provided to a user of a mobile device when interacting with the medical care application portal whose operation is discussed with respect to FIG. 7.

Figure 3:
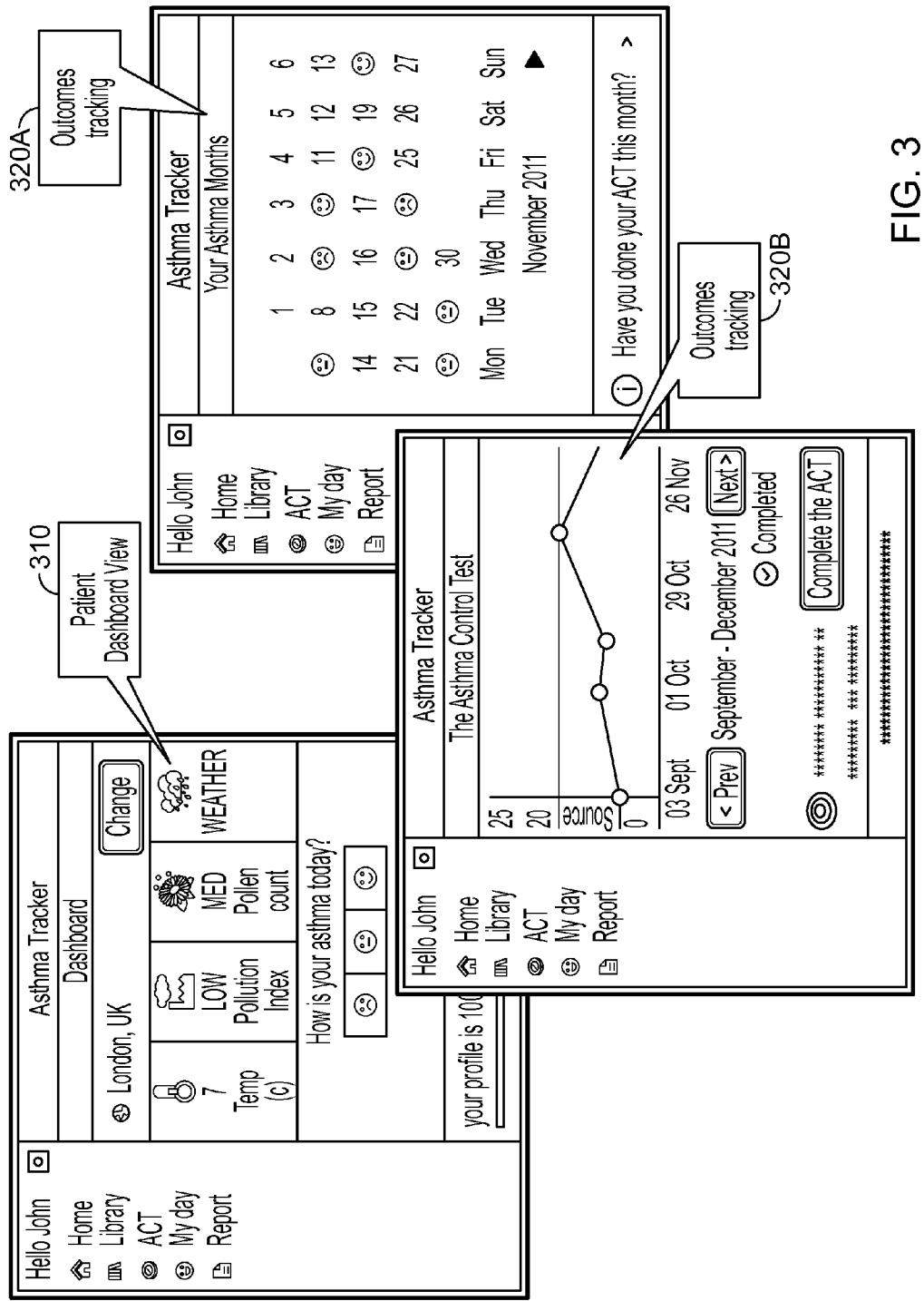
FIG. 3 illustrates a series of views that shows how a patient may manage asthma symptoms.

FIG. 3 illustrates a series of views that shows how a patient may manage asthma symptoms. FIG. 3 presents three views of an asthma management app. Patient dashboard view 310 presents information about environmental factors that may affect asthma, including temperature, pollution, pollen counts, and weather. The user is allowed to enter a "state" of the patient in responding to asthma at a given time. The states provided here are a happy, neutral or sad emoticon that indicates how the user judges the severity of his or her asthma. The results may demonstrate an "outcomes" tracking section where a patient may measure their progress. In one possible "outcomes" tracking section 320A, the results displayed over a calendar so that a patient may measure their outcomes or so that a physician may perceive the outcomes for a patient and/or a population (or subset of a population as sorted by demographic, condition, treatment regimen, age, gender, location, or profile). In another possible "outcomes" tracking section 320B, the results are plotted as a line graph over time to track how the severity of the asthma changes over time.

Figure 4:
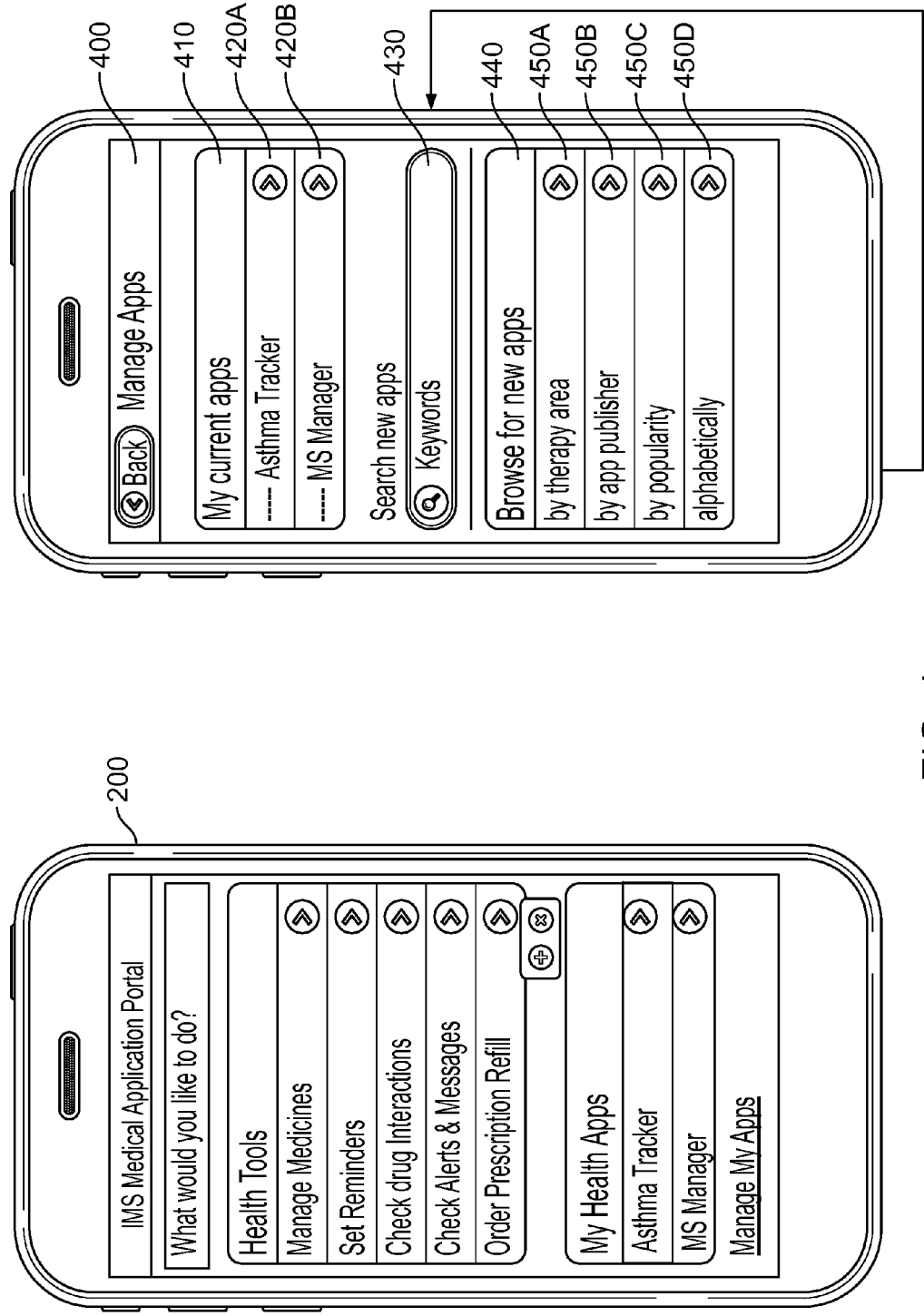
FIG. 4 demonstrates how a medical care application may interface with subordinate applications so that the medical care application may establish an interface to coordinate the exchange of health care information.

FIG. 4 demonstrates how a medical care application may interface with subordinate applications so that the medical care application may establish an interface to coordinate the exchange of health care information. Manage Apps 400 may be accessed from Manage My Apps 260 in FIG. 2. In one configuration, the subordinate application is prescribed by a physician to permit a patient on a wireless device to both receive the prescription pharmaceutical compound and also access an associated subordinate application. Manage Apps 400 lists My current apps 410. The examples are once again Asthma Tracker 420A and MS Manager 420B. By selecting these applications, these applications can launch. Note that these applications may be provided in conjunction with branded treatments. For example, Asthma Tracker 420A may be provided in association with a branded asthma drug and MS Manager 420B may be provided in association with a branded MS drug. Alternatively, and as shown in FIG. 4, the user may browse for additional subordinate applications that interface with the master application. The user may enter keywords 430 to search for new apps. Alternatively, the user may browse for new apps 440 from a selection hierarchy. The selection hierarchy may be organized by therapy area 450A, by application publisher 450B, by popularity 450C, or alphabetically 450D. Authorization from a physician, pharmacist and/or other licensed professional may be required in order for the user to access the subordinate application and/or portions of the subordinate application.

Manage My Apps 260 may optionally include other functionality besides simple addition and removal of apps, such as changing settings or managing financial transactions related to apps such as, if it is necessary to purchase an application or pay a monthly fee for use of an app.

However, FIG. 4 simply illustrates the user's perspective of how interaction and distribution of applications is handled. Additional information related to the distribution of applications, information interchange between apps, and data gathering and analytics will be discussed in connection with FIG. 7, below.

Figure 5:
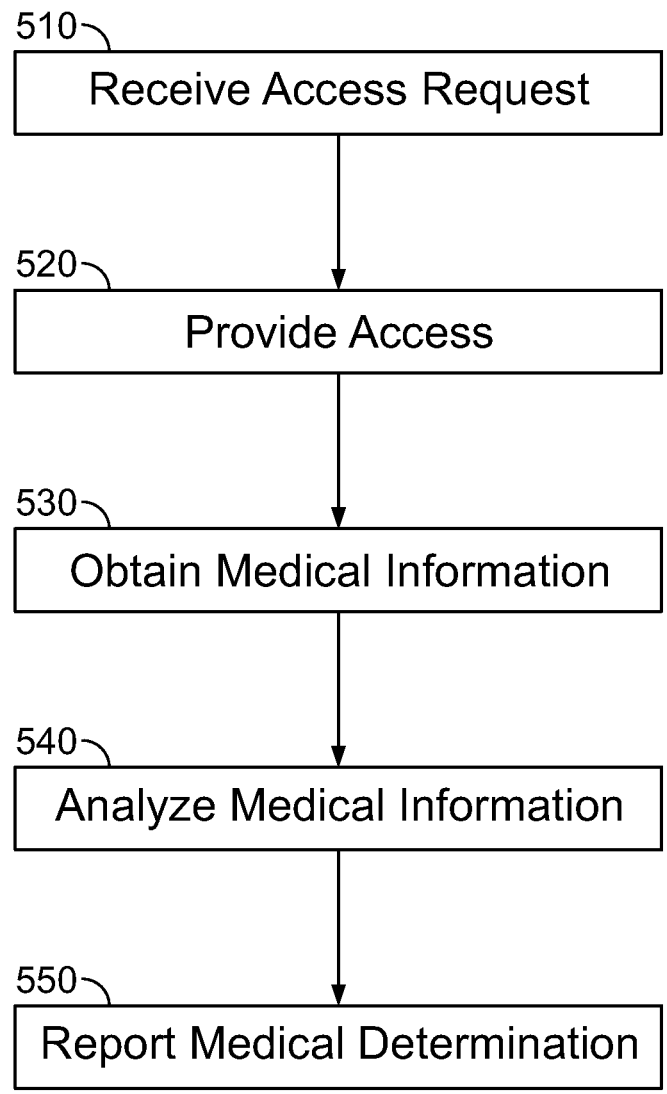
FIG. 5 is a flow chart of a process by which a medical care applications portal exchanges information with a mobile computing device.

FIG. 5 is a flow chart of a process by which a medical care applications portal exchanges information with a mobile computing device.

At block 510, a request to access to a medical care application at a medical care application portal for a user of a mobile computing device is received. Client 140 may request access to an "application store" or receive a QR code from a physician or pharmacist to load a web site that facilitates access to an application. Thus, a patient may request access to a medical care application of interest themselves, or an access request to a medical care application may be made on their behalf, such as by a physician, pharmacist, pharmaceutical company, insurance provider, or another party that has a reason to believe that the application is relevant to the patient. Such an application store may be hosted by computing system 100, or alternatively by other appropriate infrastructure, such as one or more appropriately configured web servers.

At block 520, access is provided for the user of the mobile computing device to the medical care application by the medical care application portal. For example, the medical care application portal may permit a mobile computing device to download a medical care application associated with a particular pharmaceutical compound or monitor a particular medical condition. The portal may also provide access to the medical care application online, such as by a web page in a web browser. In general, as discussed above, applications may reside at the mobile device, at a server, or may be distributed, such that various ways exist for the medical care application portal to enable access by the user to the medical care application.

At block 530, medical information relevant to the user is obtained, such that at least a portion of the medical information is received as input from the user via the medical care application. Client 140 may provide information to computing system 100 by entering information in the application. Such information may include information about asthma severity, as illustrated in FIG. 3. However, the information may also include information from sensors, such as temperature or pollution information, or information from other entities such as retail prescription data 110, longitudinal prescription data 112, reference prescriber data 114, and pharmaceutical purchase data 116, as discussed with respect to FIG. 1.

At block 540, the medical information is analyzed to make a medical determination related to the user. The analysis process is discussed above, and involves processing the medical information using data processing module 110 and possibly statistical ranking module 120 to process the data. As noted previously, information about client 140 may be compared to aggregated measures from other medical data, such as averages.

At block 550, the medical determination is reported to a medical decision maker for further action, via the medical care application. In this context, a medical decision maker may include a variety of potential parties that may make decisions regarding the user's course of treatment. However, medical determinations are only one type of determination that may be made, and alternative types of determinations that may be made will be discussed in connection with the alternative implementation discussed with respect to FIG. 7. The patient himself or herself is considered to be a medical decision maker in most cases, as the patient may make health care choices based on the medical determination. However, other parties may operate in the role of medical decision maker. For example, for a patient who is a child, the child's parents or guardian may be a medical decision maker. Additionally, medical decision makers may include doctors, nurses, pharmacists, and other health care professionals, and also potentially insurance providers. By reporting the medical determination to a medical decision maker, the medical decision maker may take appropriate actions to advance the patient's medical care. The reporting may be performed by reporting module 122. For example, the medical determination may be a suggestion the patient make a medical appointment or alter a plan of care. The medical determination may also include a determination that the user should access a medical care application to treat a medical condition. For example, an implementation may recommend a blood pressure tracking application to a doctor to suggest to a patient who has hypertension.

Figure 6:
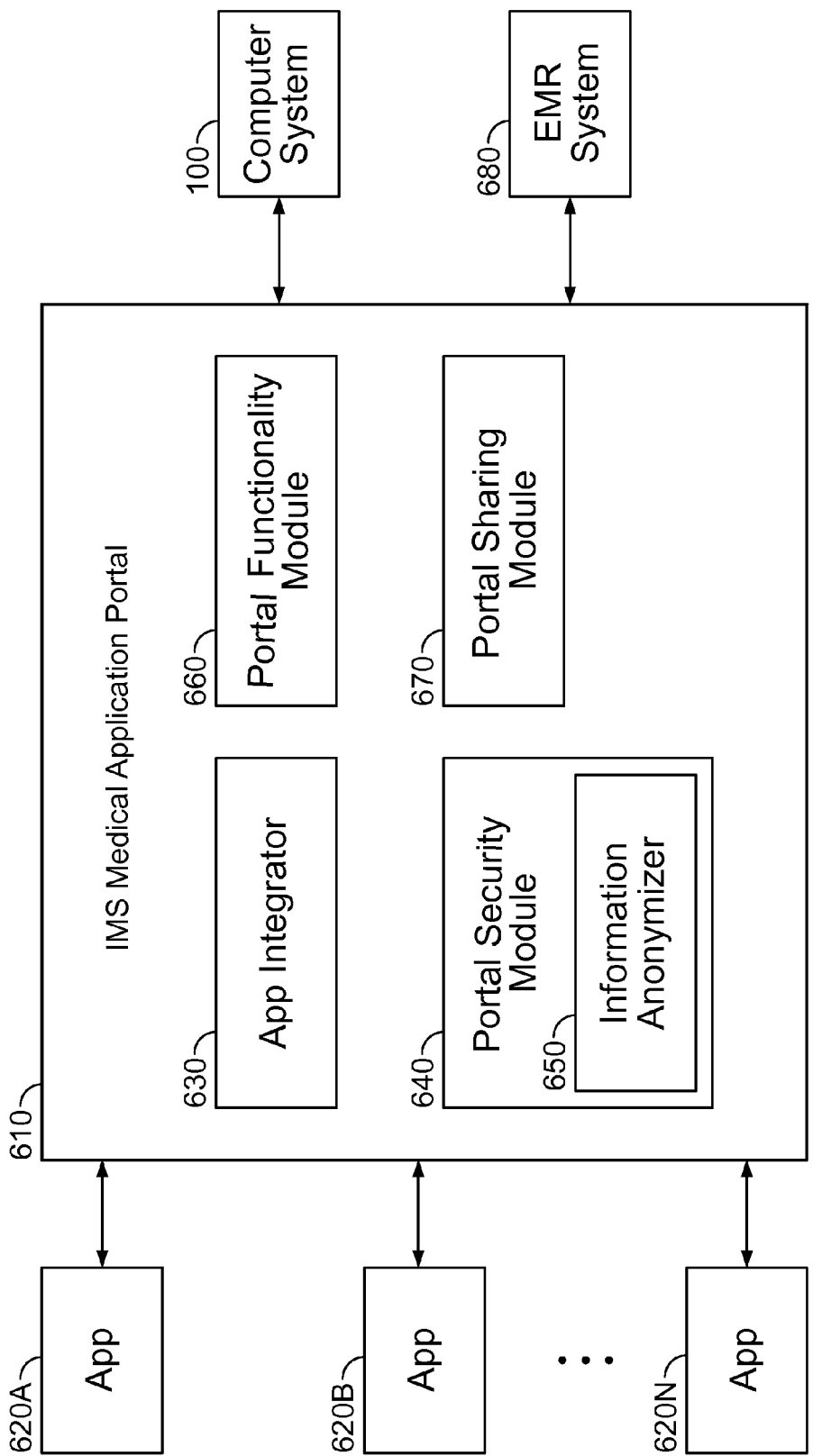
FIG. 6 is a block diagram illustrating an example system for managing secure information exchange between applications at a mobile device.

FIG. 6 is a block diagram illustrating an example system for managing secure information exchange between applications at a mobile device. For example, such a system may include a module, IMS Medical Application Portal 610, that manages secure information exchange between applications at a mobile device. IMS Medical Application Portal 610 itself, in certain implementations, may be hosted at the mobile device or it may be accessed by a web portal. IMS Medical Application Portal 610 is an application with built-in functionality, but it is not just a single application. IMS Medical Application Portal 610 is a secure mobile environment that integrates third-party applications on a safe and secure environment. It allows the secure sharing of sensitive health information across applications. Furthermore, it connects directly to electronic medical records (EMR) systems, and not just via e-mail, to promote information exchange. Additionally, IMS Medical Application Portal 610 can act as an information gateway to receive medical data and route that data between apps.

The medical data that is routed may be obtained from one or more apps 620A, 620B . . . 620N. IMS Medical Application Portal 610 may have a variety of components that help facilitate the information interchange. These components may include modules consisting of appropriate software and/or hardware to perform their designated functions. IMS Medical Application Portal 610 may include an app integrator 630, a portal security module 640, a portal functionality module 660, and a portal sharing module 670. Portal security module 640 may further include an information anonymizer 650. IMS Medical Application Portal 610 may further communicate with computer system 100 as described in FIG. 1. IMS Medical Application Portal 610 may also have the capability to directly interface with an EMR system 680 to allow access to medical information in an efficient manner.

App integrator 630 manages integrating one or more apps 620A, 620B . . . 620N into IMS Medical Application Portal 610. App integrator 630 ensures that the user can access and interact with appropriate apps that meet his or her needs. Additionally, portal security module 640 ensures that the medical data operated upon by IMS Medical Application Portal 610 remains secure. As discussed above, portal security module 640 ensures that privacy and security requirements are respected, so that individual apps cannot access information that they should not and data remains secure as the apps share it with one another. Part of the operation of portal security module 640 may optionally be performed by information anonymizer 650, which may filter the information provided by apps 620A, 620B . . . 620N to ensure that no app should receive information that it is not entitled to receive.

IMS Medical Application Portal 610 may also include a portal functionality module 660. Portal functionality module 660 provides the basic functions of IMS Medical Application Portal 610, such as health tools depicted as items 220 and 230A-E on FIG. Additionally, IMS Medical Application Portal 610 may include a portal sharing module 670. Portal sharing module 670 manages data interchange between apps. For example, it manage data interchange by gathering and storing information centrally that it receives from app 620A, and if portal security module 640 indicates that it is proper to do so, share information with another app 620B subsequently.

Figure 7:
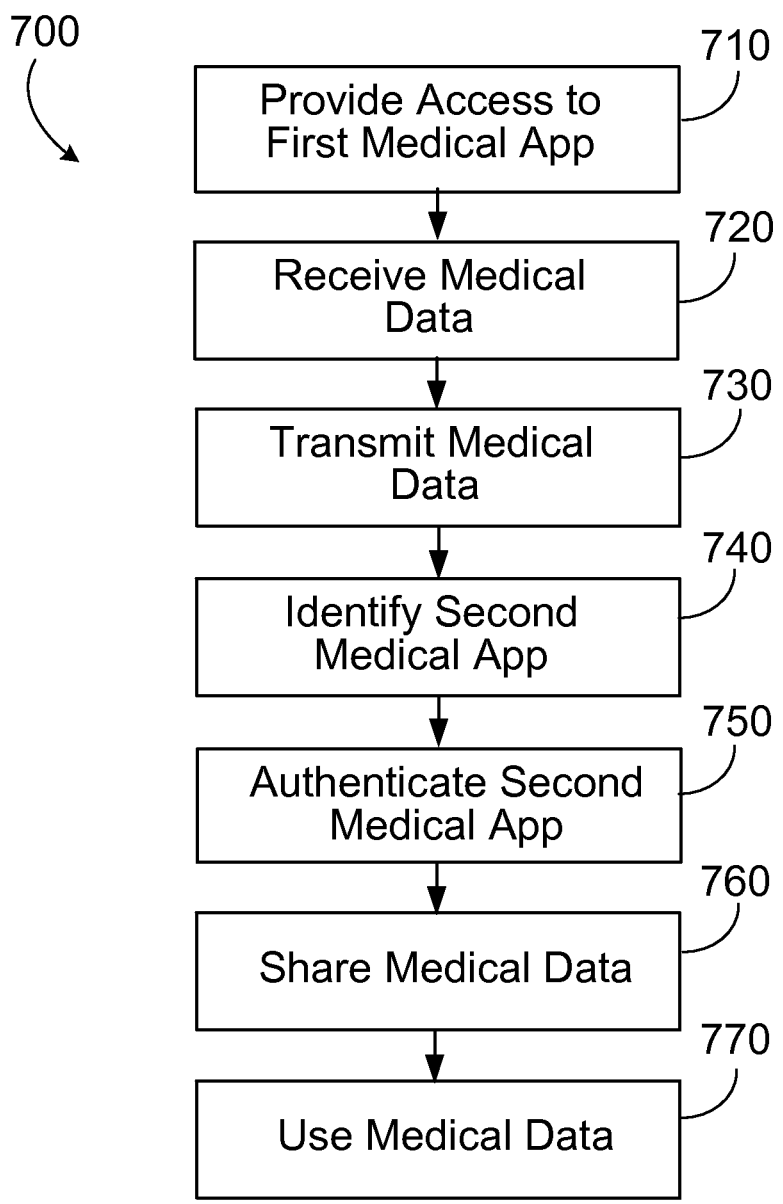
FIG. 7 is a flow chart of a process by which a medical care applications portal manages access to and secure information interchange between multiple medical care applications.

FIG. 7 is a flow chart of a process by which a medical care applications portal manages access to and secure information interchange between multiple medical care applications.

At block 710, an implementation provides access to a first medical application. More specifically, a user is provided with access to a first medical application on a mobile device, wherein the application is relevant to a medical condition of the user. It should be noted that the first medical application may be chosen as being relevant to a specific medical condition of the user, such as hepatitis or cystic fibrosis, or the general medical condition of the user, which may include the user's overall health. An example of how this step may occur is illustrated at FIGS. 2-3. A medical application portal may provide access for a user to a medical application. For example, IMS Medical Application Portal 200 may facilitate access for a user to a specific application, such as Asthma Tracker 250A. Access by the user to Asthma Tracker 250A is illustrated through some sample screenshots in FIG. 3. The portal may provide access to the first medical application in a variety of ways. The portal may download the medical application to a client device. Alternatively, the medical application may be provided in a web browser, such as through a plug-in or through scripting technology. An additional aspect of this part of the process of an implementation is that in general, the application is chosen for the user by a health care professional as being relevant to a medical condition of the user. For example, a user's neurologist might prescribe MS Manager 250B for use by a user. However, health care applications may be prescribed by other health care providers, as well as other professionals involved in the health care process. It may also be noted that in a variant of this method implementation, it is certainly possible that a user may choose a medical application on their own to address a medical condition with which they are diagnosed. For example, FIG. 4 shows a part of the user interface of IMS Medical Application Portal that allows the user to "Browse for new apps" 440, "by therapy area" 450A, "by app publisher" 450B, "by popularity" 450C, or "alphabetically" 450D. Thus, FIG. 4 shows an implementation in which the user selects the application, and is not merely assigned the application by the health care professional.

At block 720, an implementation receives medical data. More specifically, medical data is received from the user, wherein at least a portion of the medical data is received from the user via the first medical application at an information gateway provided by the mobile device, the medical data comprising private information relevant to the medical condition. The way in which medical data is received may vary from application to application, and from implementation to implementation. At least a part of the medical data may be received from the user via the application. Such data is generally received by information exchange between the user and the mobile device. For example, the user may use a variety of input devices, such as a keyboard, touchscreen, microphone, control buttons, and so on to provide input into an interface provided by the application. However, the application may also be fully capable of receiving medical data by other means. For example, it may be possible for the user to instruct the medical application to access files, such as electronic medical records, that include information that is relevant to the medical care for the user. Other medical information may be provided by a retail pharmacy, a doctor, or a pharmaceutical company. Additionally, medical information may be derived from sensors that gather information about the physical status of the users. These sensors may provide diagnostic data about the user, such as blood pressure, temperature, blood oxygen, and so forth. Medical information may also include information from laboratory procedures, such as analysis of a blood sample or urine sample, or a laboratory test for a medication level or the presence of an infectious disease. Also, the medical information should at least include some private data, as implementations are designed to protect such data. While it is certainly possible to envision an implementation which only includes private data, or only non-private data, it is important that implementations are aware of which data should be accessible to anyone, and manage which data should have restricted access and who should be able to access that data.

At block 730, an implementation transmits medical data. More specifically, the medical data to a secure information repository for subsequent use in generating a conclusion related to the medical condition of the user. As discussed above, the medical data was received from the user via the first medical application at block 720. In the context of FIG. 1, this step can be implemented by client 140 which hosts IMS Medical Application Portal 200 transmitting the medical data to storage device 124. However, the details of how the medical data is stored may vary from implementation to implementation. An aspect of the storage that is necessary is that the storage must be able to protect the privacy of the private parts of the data. Thus, when access to the data is subsequently requested, the secure information repository should provide any public data to any requester, but only a properly authenticated part should have access to the private data.

At block 740, an implementation identifies a second medical application. More specifically, a second medical application is identified that that is relevant to the medical condition of the user. The second medical application may be identified by a variety of parties, as discussed above with respect to block 710, such as by the patient him or herself. In one implementation, the application is identified as being related to a medical condition of the user. However, variants are possible. For example, the application may be identified based on other information germane to the user's health care, such as a medication the user takes, a medical device the user uses, or a type of medical practitioner the user has dealt with. Alternatively, the choice of the second medical application may be based on the identity of the first medical application or on information gathered from the first medical application. For example, the first medical application may be a diabetes management suite, and laboratory results gathered by that application may suggest a need for an application to track administration of a hypertension drug.

At block 750, an implementation authenticates the second medical application. More specifically, a second medical application is authenticated to provide access for the second medical application to the medical data at the secure information repository. In this stage, the second medical application receives and then uses information that it is legitimately entitled to access private information on behalf of the user. This may include information such as a login and password to a user account, identifying information such as SSN or birthdate, or other authenticating information such as a swipe pattern or biometric authentication such as fingerprint, voiceprint or retinal scan identification. Authentication may also involve encryption, such as public-key or private-key encryption, that can establish a secure connection for information accessed by the second medical application. The authentication will generally provide the second medical application with access to the user's public information, as well as at least a part of the private information.

At block 760, an implementation shares medical data. More specifically, the medical data is shared with the authenticated second medical application. As discussed, the second medical application by this stage has established that it is entitled to a certain portion of the user's medical data, and may have taken steps such as encryption to help ensure that when the medical data is shared third-parties that are not entitled to access the data cannot eavesdrop and obtain improper access to the data. In general, this step operates such that the second medical application requests medical data from the secure information repository as part of its operation. Hence, if the first medical application stored readings from blood sugar levels that the user took, the second medical application can subsequently access that information and use it in the context of another application.

At block 770, an implementation uses the medical data. More specifically, the medical data is used by the second medical application to generate a conclusion related to the medical condition of the user. The conclusion can be a factual conclusion or a recommendation. The conclusion may be a conclusion that aids in the treatment of the medical condition of the user. For example, the conclusion may be one of: a diagnosis, a determination that a user should begin a particular therapy, a determination that a user should cease a particular therapy, a determination that the user should alter a plan of care, a determination that the user should access a medical care application to treat a medical condition, or a determination that the user should schedule an appointment with a medical professional. For example, the conclusion may provide information to aid in the treatment of the medical condition of the user. As another example, the application may suggest a variety of medical interventions, such as use of a drug or medical device, a change of diet, a laboratory procedure, a medical appointment, a surgery, and so on.

However, implementations may use the medical data for a wide variety of purposes, and the use of the medical data need not be exclusively limited simply to providing diagnoses or treatment recommendations. Indeed, as has been discussed extensively throughout this application, the medical data may be used by an application such as the second medical application to take advantage of many helpful conclusions that can be derived from the medical data, both with respect to that specific user and with respect to larger populations to which the user belongs. For example, such conclusions may be used to help make business decisions.

Thus, while privacy concerns need to be respected, medical data about individual users can be used not only for treatment, but also for other purposes including medical and pharmaceutical research, and also other applications ranging from law enforcement to marketing. Additionally, it is possible to compare medical data for individual users to medical data that has been aggregated for groups of users. While this approach has been discussed above, it is possible to aggregate data for populations of users, and obtain statistics such as various averages or other metrics about the population, and derive conclusions based on such comparisons. Examples of such uses of the data have been discussed above. In general, while implementations may use the medical data and its context to improve medical care recommendations and outcomes, that is not the only use of the medical data and implementations should be understood to include any use of the medical data that is helpful to a participant in the health care process, that may be provided by the operation of the second medical application on the medical data.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible nontransitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS)

receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

Pharmaceuticals in various implementations need not necessarily be heavily controlled, and the methods presented herein equally apply to over-the-counter drugs or even potentially to herbal preparations or nutritional supplements that have the potential to have an impact on medical treatment. The use of St. John's Wort to treat a patient with clinical depression may be considered by an implementation, as may a nutritional supplement such as fish oil or a prescription antidepressant.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method performed by a medical care application portal, the method comprising:
    receiving, at the medical care application portal, data regarding a medical condition of a user, wherein a portion of the data is generated by the first medical application at a mobile device of the user based on measurements from a biometric sensor on the mobile device of the user and wherein the medical care application portal manages access to the data regarding the medical condition of the user from more than one medical care applications on the mobile device of the user;

in response to receiving the data regarding the medical condition of the user, identifying a second medical application configured to manage the medical condition of the user and downloadable for installation on the same mobile device of the user, wherein the second medical application is different from the first medical application and is not configured to access the portion of the data based on measurements from the biometric sensor on the mobile device directly from the first medical application at the mobile device;

in response to identifying the second medical application configured to manage the medical condition of the user, providing a recommendation to the mobile device of the user for the user to use the second medical application on the mobile device;

authenticating the second medical application based on authentication information received from the user through the second medical application on the mobile device of the user, the authentication information including information indicating that the second medical application has been prescribed by a healthcare professional for the user of the mobile device;

determining whether the portion of the data generated by the first medical application at the mobile device of the user based on measurements from the biometric sensor should be accessible to the authenticated second medical application;

in response to determining that the portion of the data generated by the first medical application at the mobile device of the user based on measurements from the biometric sensor should be accessible to the authenticated second medical application, granting the second medical application on the mobile device of the user access to the data regarding the medical condition including the portion of the data generated by the first medical application at the mobile device of the user based on measurements from the biometric sensor on the mobile device of the user such that a conclusion related to the medical condition of the user is generated by the second medical application in response to the user's inquiry at the second medical application; and in response to determining that the portion of the data generated by the first medical application at the mobile device of the user based on measurements from the biometric sensor should not be accessible to the authenticated second medical application, denying the second medical application on the mobile device access to the data generated by the first medical application at the mobile device of the user based on measurements from the biometric sensor on the mobile device of the user.

2. The computer-implemented method of claim 1, wherein the conclusion is a conclusion that aids in the treatment of the medical condition of the user.

3. The computer-implemented method of claim 2, wherein the conclusion comprises one of: a diagnosis, a determination that a user should begin a particular therapy, a determination that a user should cease a particular therapy, a determination that the user should alter a plan of care, a determination that the user should access a medical care application to treat a medical condition, or a determination that the user should schedule an appointment with a medical professional.

4. The computer-implemented method of claim 1, wherein the conclusion includes information that helps a participant in the health care process to make a business decision.

5. The computer-implemented method of claim 1, wherein the conclusion is generated at least in part by comparing the data regarding the medical condition for the user to de-identified aggregated medical data obtained for other users regarding the same medical condition and stored at the medical care application portal.

6. The computer-implemented method of claim 1, wherein the first medical care application is associated with a particular pharmaceutical compound, a particular medical condition, a particular pharmaceutical manufacturer, or a particular health care professional.

7. The computer-implemented method of claim 1, wherein at least a portion of data regarding the medical condition is received at the medical care application portal from at least one of: an electronic medical records system, a medical claims records system, a retail pharmacy records system, a health care professional records system, a pharmaceutical company records system or a sensor communicatively coupled to the mobile computing device.

8. A system comprising:
one or more computers and one or more storage devices storing instructions that are operable, when executed by the one or more computers, to cause the one or more computers to perform operations comprising:

receiving, at the medical care application portal, data regarding a medical condition of a user, wherein a portion of the data is generated by the first medical application at a mobile device of the user based on measurements from a biometric sensor on the mobile device of the user and wherein the medical care application portal manages access to the data regarding the medical condition of the user from more than one medical care applications on the mobile device of the user;

in response to receiving the data regarding the medical condition of the user, identifying a second medical application configured to manage the medical condition of the user and downloadable for installation on the same mobile device of the user, wherein the second medical application is different from the first medical application and is not configured to access the portion of the data based on measurements from the biometric sensor on the mobile device directly from the first medical application at the mobile device;

in response to identifying the second medical application configured to manage the medical condition of the user, providing a recommendation to the mobile device of the user for the user to use the second medical application on the mobile device;

authenticating the second medical application based on authentication information received from the user through the second medical application on the mobile device of the user, the authentication information including information indicating that the second medical application has been prescribed by a healthcare professional for the user of the mobile device;

determining whether the portion of the data generated by the first medical application at the mobile device of the user based on measurements from the biometric sensor should be accessible to the authenticated second medical application;

in response to determining that the portion of the data generated by the first medical application at the mobile device of the user based on measurements from the biometric sensor should be accessible to the authenticated second medical application, granting the second medical application on the mobile device of the user access to the data regarding the medical condition including the portion of the data generated by the first medical application at the mobile device of the user based on measurements from the biometric sensor on the mobile device of the user such that a conclusion related to the medical condition of the user is generated by the second medical application in response to the user's inquiry at the second medical application; and in response to determining that the portion of the data generated by the first medical application at the mobile device of the user based on measurements from the biometric sensor should not be accessible to the authenticated second medical application, denying the second medical application on the mobile device access to the data generated by the first medical application at the mobile device of the user based on measurements from the biometric sensor on the mobile device of the user.

9. The system of claim 8, wherein the conclusion is a conclusion that aids in the treatment of the medical condition of the user.

10. The system of claim 9, wherein the conclusion comprises one of: a diagnosis, a determination that a user should begin a particular therapy, a determination that a user should cease a particular therapy, a determination that the user should alter a plan of care, a determination that the user should access a medical care application to treat a medical condition, or a determination that the user should schedule an appointment with a medical professional.

11. The system of claim 8, wherein the conclusion includes information that helps a participant in the health care process to make a business decision.

12. The system of claim 8, wherein the conclusion is generated at least in part by comparing the data regarding the medical condition for the user to de-identified aggregated medical data obtained for other users regarding the same medical condition and stored at the medical care application portal.

13. The system of claim 8, wherein the first medical care application is associated with a particular pharmaceutical compound, a particular medical condition, a particular pharmaceutical manufacturer, or a particular health care professional.

14. The system of claim 8, wherein at least a portion of data regarding the medical condition is received at the medical care application portal from at least one of: an electronic medical records system, a medical claims records system, a retail pharmacy records system, a health care professional records system, a pharmaceutical company records system or a sensor communicatively coupled to the mobile computing device.

15. A non-transitory computer-readable medium storing software comprising instructions executable by one or more computers which, upon such execution, cause the one or more computers to perform operations comprising:

receiving, at the medical care application portal, data regarding a medical condition of a user, wherein a portion of the data is generated by the first medical application at a mobile device of the user based on measurements from a biometric sensor on the mobile device of the user and wherein the medical care application portal manages access to the data regarding the medical condition of the user from more than one medical care applications on the mobile device of the user;

in response to receiving the data regarding the medical condition of the user, identifying a second medical application configured to manage the medical condition of the user and downloadable for installation on the same mobile device of the user, wherein the second medical application is different from the first medical application and is not configured to access the portion of the data based on measurements from the biometric sensor on the mobile device directly from the first medical application at the mobile device;

in response to identifying the second medical application configured to manage the medical condition of the user, providing a recommendation to the mobile device of the user for the user to use the second medical application on the mobile device;

authenticating the second medical application based on authentication information received from the user through the second medical application on the mobile device of the user, the authentication information including information indicating that the second medical application has been prescribed by a healthcare professional for the user of the mobile device;

determining whether the portion of the data generated by the first medical application at the mobile device of the user based on measurements from the biometric sensor should be accessible to the authenticated second medical application;

in response to determining that the portion of the data generated by the first medical application at the mobile device of the user based on measurements from the biometric sensor should be accessible to the authenticated second medical application, granting the second medical application on the mobile device of the user access to the data regarding the medical condition including the portion of the data generated by the first medical application at the mobile device of the user based on measurements from the biometric sensor on the mobile device of the user such that a conclusion related to the medical condition of the user is generated by the second medical application in response to the user's inquiry at the second medical application; and in response to determining that the portion of the data generated by the first medical application at the mobile device of the user based on measurements from the biometric sensor should not be accessible to the authenticated second medical application, denying the second medical application on the mobile device access to the data generated by the first medical application at the mobile device of the user based on measurements from the biometric sensor on the mobile device of the user.

16. The medium of claim 15, wherein the conclusion is a conclusion that aids in the treatment of the medical condition of the user.

17. The medium of claim 16, wherein the conclusion comprises one of: a diagnosis, a determination that a user should begin a particular therapy, a determination that a user should cease a particular therapy, a determination that the user should alter a plan of care, a determination that the user should access a medical care application to treat a medical condition, or a determination that the user should schedule an appointment with a medical professional.

18. The medium of claim 15, wherein the conclusion includes information that helps a participant in the health care process to make a business decision.

19. The medium of claim 15, wherein the conclusion is generated at least in part by comparing the data regarding the medical condition for the user to de-identified aggregated medical data obtained for other users regarding the same medical condition and stored at the medical care application portal.

20. The medium of claim 15, wherein the first medical care application is associated with a particular pharmaceutical compound, a particular medical condition, a particular pharmaceutical manufacturer, or a particular health care professional.

21. The medium of claim 15, wherein at least a portion of data regarding the medical condition is received at the medical care application portal from at least one of: an electronic medical records system, a medical claims records system, a retail pharmacy records system, a health care professional records system, a pharmaceutical company records system or a sensor communicatively coupled to the mobile computing device.

* * * * *